United States Patent [19]
Fox et al.

[11] Patent Number: 5,578,661
[45] Date of Patent: Nov. 26, 1996

[54] GEL FORMING SYSTEM FOR USE AS WOUND DRESSINGS

[75] Inventors: Adrian S. Fox, Monroe, N.Y.; Amy E. Allen, Stamford, Conn.

[73] Assignee: Nepera, Inc., Harriman, N.Y.

[21] Appl. No.: 221,159

[22] Filed: Mar. 31, 1994

[51] Int. Cl.$^6$ .............. C08L 5/00; C08L 39/06; C08L 71/02
[52] U.S. Cl. ............ 524/027; 524/29; 525/54.2; 525/203; 525/221; 514/944
[58] Field of Search ............ 524/27, 29; 525/54.2, 525/203, 221; 514/944

[56] References Cited

U.S. PATENT DOCUMENTS

| | | | |
|---|---|---|---|
| 3,419,006 | 12/1968 | King | 128/268 |
| 4,619,995 | 10/1986 | Hayes | 536/20 |
| 4,699,146 | 10/1987 | Sieverding | 128/640 |
| 4,706,680 | 11/1987 | Keusch | 128/640 |
| 4,920,158 | 4/1990 | Murray et al. | 524/29 |
| 4,989,607 | 2/1991 | Keusch | 128/640 |
| 5,143,071 | 9/1992 | Keusch | 128/640 |
| 5,318,780 | 6/1994 | Viegas et al. | 424/427 |
| 5,420,197 | 5/1995 | Lorenz et al. | 525/54.3 |

OTHER PUBLICATIONS

International Specialty Products (ISP), "Acrylidone™ Anionic Polymers", 1991.
Nova Chem Ltd., "N,O—Carboxymethylchitosan is NOCC", 1991.
Presented at the 4th International Conference on Chitin and Chitosan, "N,O—Carboxymethyl Chitosan, A New Water Soluble Chitin Derivative", Davies et al., Aug. 1988.
"Acrylidone Anionic Copolymers", by John C. Hornby, Ph.D. et al., Soap/Cosmetics/Chemical Specialties, Jun. 1993.
GAF Corporation, "Gantrez® An Copolymer Poly (Methyl Vinyl Ether/Maleic Anhydride)", 1983.
GAF Corporation, "Polyplasdone XL® Polyplasdone®XL–10, Crospovidone NF, Tablet Disintegrants Crosslinkd, insoluble homopolymers of N–vinyl–2–pyrrolidone for use in the manufacture of pharmaceuticals", 1984.

*Primary Examiner*—Thomas Hamilton, III
*Attorney, Agent, or Firm*—Pennie & Edmonds

[57] ABSTRACT

A gel forming system comprising an aqueous mixture of a first component of at least one water-soluble polymer in an amount sufficient to increase the initial viscosity of the mixture and impart adhesivity properties thereto; a second component of a acid-containing polymer; a third component of an amino-containing polymer; and water. This system has a pH in the range of between about 5.5 and 8.5 and the second and third components are each present in sufficient amounts which, in combination, increase the cohesiveness of the mixture over time, such that the mixture can be initially combined in a relatively fluid state and subsequently forms a cohesive gel structure. This system is useful as a wound dressing for deep wound cavities because the gel protects the wound and permits healing, does not interfere with new tissue growth or development, is capable of absorbing significant amounts of wound exudate, and has sufficient cohesive strength for subsequent removal from the cavity as an integral plug without interrupting the healing process.

31 Claims, No Drawings

GEL FORMING SYSTEM FOR USE AS WOUND DRESSINGS

TECHNICAL FIELD

This invention relates to compositions of polymer mixtures which are relatively fluid for dispensing into a wound bed or cavity and which are capable of forming a gel therein. The gel is preferably a hydrogel which protects the wound and permits healing, does not interfere with new tissue growth or development, is capable of absorbing significant amounts of wound exudate, and has sufficient cohesive strength for subsequent removal from the cavity or bed as an integral plug without interrupting the healing process.

BACKGROUND OF THE INVENTION

Hydrophilic gels that contain up to 95 percent water have been known for some time. Some of the early hydrogels were prepared by irradiation crosslinking and exhibited smooth, non-tacky surfaces. Later developments included hydrogels having interesting surface characteristics, such as adhesiveness, tackiness or non-stringiness. These hydrophilic gels can be manufactured into different forms including sheets and a number of applications have been disclosed which utilize their unique characteristics. U.S. Pat. No. 5,143,071 lists a number of such hydrogels and specifically discloses polyvinyl pyrrolidone and polyethylene oxide hydrogels formed from aqueous solutions which are crosslinked by radiation dosages of 0.5 to 4.5 Mrads.

Many of these hydrogels are used as wound dressings. In one embodiment, the hydrogel is used as a film which acts as a barrier to protect the wound from external contamination, thus promoting healing. Water soluble drugs can be added to these films and these drugs can migrate though the hydrogel film without disruption of the film's bacterial barrier properties (See, e.g., U.S. Pat. No. 3,419,006). A number of hydrogel sheets adapted for use in medical electrode applications are produced commercially, wherein the use of electric current enhances the transfer of the drug through the film.

Although many examples of hydrogels and resulting products, such as medical electrode assemblies, are known, these prior materials suffer from one or more undesirable characteristics that limit or, in some cases, preclude their utility as wound dressings, drug delivery systems, medical electrodes or the like. In particular, these previous materials can dry out rapidly, become brittle when cooled or easily lose their adhesive surface characteristics with the slightest over-exposure to crosslinking radiation.

There is a need for hydrogel products which overcome the disadvantages of the prior art. In particular, there is a need for deep wound dressings, such as for treatment of ulcers, in the form of flexible, non-stringy, cohesive hydrogels which can be applied in a relatively fluid state and which forms a gel within the wound cavity to protect the wound and promote healing and which can later be removed as an integral component without affecting the healing process. The present invention provides a number of compositions which can satisfy this need.

SUMMARY OF THE INVENTION

The present invention relates to a gel forming system comprising an aqueous mixture of a first component of at least one water-soluble polymer in an amount sufficient to increase the initial viscosity of the mixture and impart adhesivity properties thereto; a second component an acid-containing polymer; a third component of a polysaccharide or amino-containing polymer; and water. This system has a pH in the range of between about 5.5 and 8.5 and the second and third components are each present in sufficient amounts which, in combination, increase the cohesiveness of the mixture over time, such that the mixture can be initially combined in a relatively fluid state and subsequently forms a cohesive gel structure.

The first component is preferably a hydrophilic water-soluble polymer of polyethylene oxide, polyvinylpyrrolidone or mixtures thereof and is advantageously present in an amount of between about 3 and 35% by weight of the system. Especially preferred is a hydrophilic water-soluble polymer mixture of poly(vinyl pyrrolidone) and poly(ethylene oxide) in a weight ratio of between about 10/1 and 25/1 wherein the poly(vinyl pyrrolidone) is present in an amount of between about 10 and 25% by weight of the system. If desired, at least a portion of the hydrophilic water soluble polymer of the first component may be crosslinked.

The second component is advantageously present in an amount of between about 0.1 and 10% by weight of the system and contains sufficient acid or acid-forming groups to provide crosslinking capabilities or intermolecular hydrogen bonding with the first component to increase the cohesiveness of the mixture over time. This component is preferably a polymer of an acid or acid forming compound or a copolymer of an acid or acid forming compound and a monomer which forms a water soluble compound, such as is poly(vinyl pyrrolidone/acrylic acid), poly(methyl vinyl ether/maleic anhydride), poly(ethylene/maleic anhydride) or poly(acrylic acid).

If desired, a portion of the acid or acid-forming groups of the second component may be neutralized to reduce the crosslinking capabilities of the component. The acid or acid-forming groups of the second component may be neutralized by conversion to an acid salt, by conversion to an amide, or by the incorporation of anions which interfere with the hydrogen bonding capabilities of the second component.

The third component is advantageously present in an amount of between about 0.5 and 5% by weight of the system and preferably comprises a compound which contains free or substituted amino groups for accepting protons from the second component and increasing the cohesiveness of the mixture. If desired, a portion of the amino groups of the third component may be substituted with a water soluble group or a double bond to reduce the crosslinking capabilities of this component.

Preferred third components include a polysaccharide, such as those based upon glucosamine and gluconic acid derivatives, a glycosamino glycan such as heparin, alginic acid, hyaluronic acid, a carrageenan, agar, or a polyamino acid such as poly-L-lysine or a derivative thereof. The most preferred third components are chitosan derivatives such as O-carboxymethyl chitosan, N-carboxymethyl chitosan, or N,O-carboxymethyl chitosan.

The gel forming system of the present invention may also include a crosslinked hydrophilic polymer in an amount sufficient to form an interpenetrating network in the mixture. Also, one or more additional uniformly dispersed additives selected from the group consisting of preservatives, stabilizers, fire retardants, pigments, refractive particles, bactericides, antibiotics, cosmetics, moisturizers, pharmacologic agents and mixtures thereof may be present. Each additive which is included can be present at a concentration of about 0.001 to about 3% by weight of the system. Specifically preferred pharmacologic agents include EGF, PDGF or TGF-β1, since these promote wound healing.

The gel forming system may also include a humectant for increasing the solubility of the first or second components in the mixture. Preferred humectants include glycerol, propylene glycol, or poly(ethylene glycol), N-methyl pyrrolidone, N-ethyl pyrrolidone, diacetone alcohol, γ-butyryl lactone, ethyl lactate or combinations thereof, and may be present at a concentration of about 1 to 40%, preferably 5 to 20% by weight of the system.

When conductive materials are desired, the gel forming system may include a water-soluble electrolyte in an amount effective to reduce the transverse electrical resistance of the gel to an impedance at 60 Hz of less than about 1000 ohms and preferably less than about 100 ohms. This electrolyte may be an inorganic or organic salt, such as a potassium salt, a sodium salt, a magnesium salt, a calcium salt or a mixture thereof, and may be present in an amount of about 0.1 to about 10% by weight of the system.

DETAILED DESCRIPTION OF THE INVENTION

In this invention, there are three primary components which are combined with water as an aqueous mixture to provide a gel forming system: a first component of at least one water-soluble polymer in an amount sufficient to increase the initial viscosity of the mixture and impart adhesivity properties thereto; a second component of an acid-containing polymer; and a third component of a polysaccharide or amino-containing polymer.

The first component may be formed from any crosslinkable hydrophilic polymer. Preferred polymers include polymers such as polyethylene oxide ("PEO"), polyvinylpyrrolidone ("PVP"), and the like in weight percentages of about 3 to 30 percent, preferably about 4–25%, and most preferably about 5–10%. Other weight percentages of this component may be employed depending on the specific polymer or polymers used and the amount of cross-linking, if any, of the polymer or polymers. Mixtures of polymers can be used where one or more of the polymers in the mixture are crosslinked.

PEOs useful in the invention include linear, water soluble polyethylene oxides which have a weight average molecular weight ($M_w$) of 0.02–6×10$^6$ Daltons. A commercially available PEO polymer known as POLYOX (WRS N-205), having a $M_w$ of about 500 to 2000 Kilodaltons (kD) can be employed. A most preferred amount of this PEO in the formulation is 0.5 to 6%. In addition, crosslinked PEOs may be used as this component. A particularly preferred crosslinked material is 4% PEO. If desired, non-stringy hydrogels can be prepared as disclosed in U.S. Pat. No. 4,989,607 or U.S. Pat. No. 5,143,071, the content of each of which is expressly incorporated herein by reference.

When the pH of the system is below 6.5, PVP polymers are preferred because the stability of the PEO polymers is reduced. The PVP polymer is typically a polymer of N-vinyl-2-pyrrolidone having a $M_w$ of about 200 kD to about 2,000 kD. An advantageous polymer is PVP having a $M_w$ of about 1,000,000. Homogeneous aqueous mixtures comprising about 5 to about 30 weight percent of PVP are suitable in this invention. Preferred concentrations of PVP in the aqueous mixtures are about 5 to about 15 weight percent, and most preferably about 10 wt%.

PVP and PEO mixtures are advantageously utilized. In these mixtures, the weight ratio of PVP to PEO can be between about 10/1 to 30/1, preferably about 15/1 to 25/1 and most preferably about 20/1. It is also useful for the some of the polymer to be crosslinked. Conveniently, the PEO portion of the mixture can be crosslinked, since it is generally present in a smaller amount. It is also possible for a portion of the PVP to be cross-linked. Although less preferred, all of the PVP can be crosslinked. The crosslinking of PVP mixtures is described in U.S. Pat. No. 4,699,146, the disclosure of which is incorporated herein by reference.

It is also possible to utilize a crosslinked polymer in powder form, such as GAF's Polyplasdone XL or XL-10 crosslinked PVP or Union Carbide's WSR Coagulant PEO, as the first component.

The second component is a polymer which contains sufficient acid or acid-forming groups to provide crosslinking capabilities or intermolecular hydrogen bonding with the first component. This causes an increase in the cohesiveness of the mixture over time. This component is preferably a polymer of an acid, e.g., polyacrylic acid such as Carbopol P-934, or an acid forming compound such as an anhydride. Also, a copolymer of the acid or acid forming compound and a monomer which forms a water soluble compound can be used. In these copolymers, preferred acid or acid forming compounds are acrylic acid or maleic anhydride. Typical examples of these copolymers include poly(vinyl pyrrolidone/acrylic acid), poly(methyl vinyl ether/maleic anhydride) and poly(ethylene/maleic anhydride). Other copolymers which are known to one of ordinary skill in the art can instead be used, if desired.

Typical examples of commercial products include International Specialty Products' Acrylidone Anionic Copolymer 1033 or 1042 (25% vinylpyrrolidone and 75% acrylic acid), Zeeland Chemical's Ethylene Maleic Anhydride, GAF's Gantrez AN Copolymers S-95 (poly(methyl vinyl ether/maleic anhydride)—20,000 MW) and S-97 (poly(methyl vinyl ether/maleic anhydride)—70,000 MW).

It is helpful to add a cosolvent for certain of these components. For example, a small amount of glycerine is useful for solubilizing the Acrylidone Anionic Copolymer into the water of the mixture.

The polymers and copolymers which are used as the second component generally have a relatively high degree of crosslinking capability, so that small amounts are useful. If too large of an amount is used, the resulting gels will be stiff and brittle. One of ordinary skill can routinely determine the appropriate amount for any particular formulation. This component is advantageously present in an amount of between about 0.1 and 10% by weight of the system and preferably between 0.5 to 2.5%.

Alternatively, a portion of the acid or acid forming groups can be neutralized or engaged so that they will not promote crosslinking. This can be achieved by a number of different procedures. For example, a basic component such as a hydroxide can be added to this component either before or after it is added to the mixture. These basic materials will form acid salts which will not promote crosslinking. In addition, a small amount. of sodium or calcium hydroxide can be added to compounds such as Ethylene Maleic Anhydride with slight heating to reduce acid functionality.

These treatments cause the pH of the mixture to be increased to a higher value due to the buffering effect of the base. For medical uses, the pH of the resultant gels should be between about 5.5 and 8.5, and the addition of the base allows the formulations to be within this desirable range.

It is also possible to add other compounds which have groups that will tie up the acid functionality. Divalent ionic salts are useful since the anions interfere with the ability of the acid groups to promote hydrogen bonding with the other components in the mixture. One of ordinary skill in the art can envision a number of different compounds which can be used for this purpose. Calcium chloride has been found to be effective for the formulations of the examples and is preferred for that reason.

It is also possible to neutralize a portion of the acid groups by converting them to amides. This is conveniently done by reacting the first component with a compound that contains free amino groups, as would be fully understood by one of ordinary skill in the art. Thus, no further description of this treatment is necessary.

It is preferred to treat the first component with the base, salt or amino compound prior to adding it to the mixture so that it does not interfere with or crosslink the other components. For certain formulations, however, it is possible to separately add the first component and treatment agent to the mixture.

The third component preferably comprises a compound which contains free or substituted amino groups for accepting protons from the second component and increasing the cohesiveness of the mixture. A wide variety of compounds can be used as this component. Preferred third components include polysaccharides, such as those based upon glucosamine and gluconic acid derivatives, a glycosamino glycan such as heparin, alginic acid, hyaluronic acid, a carrageenan such as I or κ carrageenan, agar, or a polyamino acid such as poly-L-lysine or a derivative thereof. This component is used in an amount of between about 0.5 and 5 percent and preferably between about 2 and 3 percent by weight.

The most preferred third components are chitosan derivatives such as O-carboxymethyl chitosan, N-carboxymethyl chitosan, or N,O-carboxymethyl chitosan. These compounds and their methods of preparation are further discussed in U.S. Pat. No. 4,619,995, the content of which is expressly incorporated herein by reference thereto.

If desired, a portion of the amino groups of the third component may be substituted with a water soluble group or α,β-ethylenically unsaturated compound to reduce the crosslinking capabilities of this component. For example, an acid such as lactic acid or glycolic acid can be used to reduce the amino groups by forming amides. Thus, chitosan-lactic acid (lactate) complexes or even chitosan-hydrochloric acid complexes can be used as the third component. In addition, compounds such as glutaraldehyde can be added to the third component to tie up some of the amino groups and prevent them from crosslinking, thus reducing its crosslinking capability.

Other components can be added to the mixture. For example, one or more additional uniformly dispersed additives selected from the group consisting of preservatives, stabilizers, fire retardants, pigments, refractive particles, bactericides, antibiotics, cosmetics, moisturizers, pharmacologic agents and mixtures thereof may be present. Each additive which is included can be present at a concentration of about 0.001 to about 3% by weight of the system.

A humectant can be used to improve the physical properties of the hydrogels. The presence of humectant gives rise to a hydrogel that has a longer in-use lifetime than conventional hydrogels. This latter property is particularly desirable and advantageous because it allows longer uninterrupted medical or therapeutic treatment of an individual with fewer applications and replacement of wound dressings, electrodes, cosmetics, ultrasound coupling sheets, topical or transdermal drug delivery systems, protective drapes or other bodily contact hydrogel-based devices.

Examples of humectants that can be used in the present invention include but are not limited to glycerol, propylene glycol, poly-(ethylene glycol), N-methyl pyrrolidone, N-ethyl pyrrolidone, diacetone alcohol, γ-butyryl lactone, ethyl lactate, low molecular weight polyethylene glycol, or combinations thereof. Preferably, the humectant used in the present invention is biocompatible.

To reduce the transverse electrical resistance of the homogeneous aqueous mixtures described herein and consequently, the hydrogels which are produced therefrom, a variety of electrolytic substances may be added to the mixtures in amounts sufficient to produce conductive products. These electrolytes may be ionizable inorganic salts, organic compounds, or combinations of both. Examples of such salts include, but are not limited to, ammonium sulfate, monoethanolamine acetate, diethanolamine acetate, sodium chloride, magnesium sulfate, calcium sulfate, ammonium acetate, magnesium chloride, magnesium acetate, or combinations thereof. Preferably, the electrolyte used is stable and inert upon dissolving in the aqueous mixture and the subsequent radiation cross-linking step. Preferred salts are potassium chloride, sodium chloride, magnesium sulfate, or magnesium acetate. Potassium chloride is most preferred for EKG applications. Although virtually any amount of electrolyte may be present in the mixture, a breakdown in viscosity is observed as discussed further below, and it is preferable to have an amount of water-soluble electrolyte present at a concentration of about 0.1 to about 15 wt % of the mixture. However, the amount of electrolyte present must be effective to reduce the transverse electrical resistance of the mixture, and the resulting hydrogel, to an impedance at 10 Hz–5 MHz of less than about 1,000 ohms. Typically, about 5 wt % of an electrolyte such as potassium chloride is sufficient to reduce the impedance at 60 HZ to much less than about 100 ohms.

As noted above, the pH range of the gels should be controlled to between about 5.5 and 8.5 for certain applications. A base such as sodium or calcium hydroxide can be added to the gel to increase the pH to the desired range. Similarly, buffers such as phosphates of carbonates can be added to control the pH of the final gel product.

A wide variety of medicaments can be included in these gels. Specifically preferred medicaments or pharmacologic agents include EGF, PDGF or TGF-β1, since these promote wound healing. Other such agents which are within the level of one skilled in the art can be included for their known advantages or to achieve their particular effects.

The hydrogels produced in accordance with the invention are adhesive. These hydrogels are suitable for use, for example, as electrodes for TENS (Transcutaneous Electrical Nerve Stimulation), ESU (Electro-surgical Unit), and EKG (electrocardiogram) applications.

The adhesiveness of the gelled polymer products of the invention is sufficient to provide in the rolling ball tack test a rolling ball distance of less than about 10–30 mm while yielding an adhesion energy force in the Adhesion Energy Force ("AED") Determination Test of at least about 7 g-cm/cm$^2$, swell ratios of at least about 5, and percent gels of at least about 80. The adhesive strength of the gelled polymer product also is less than its cohesive strength. These properties enable the gelled polymer to be removed from a surface to which it is affixed without leaving a visible residue.

When a hydrogel package is ready for use as, for example, an electrode, the backing material is peeled from the package and the exposed surface of the hydrogel is applied to the skin of the patient. An electrode lead wire can be attached to the electrode at the fastener conductive member, as shown, for example, in U.S. Pat. No. 4,706,680, the content of which is expressly incorporated herein by reference thereto. Alternatively, the electrode can be provided with a lead wire already attached. The same sequence of foil removal and application of the electrode to the skin would then apply without the necessity of attaching a lead wire to the electrode before or during application.

The hydrogel component of the invention have high adhesive strengths which enables them readily to be affixed to the skin and with little risk of accidentally dropping off through loss of adhesion. Because the hydrogel is water based, it is relatively immune to the effects of moisture on the skin and will not slide off as a result of perspiration forming under the elecctrode while affixed to the skin. The hydrogels also have high cohesive strengths, which means that they can be removed from the skin after use without leaving visible residue. Interestingly, although the hydrogels have a high adhesive strength, it is not high enough to pull hairs from the skin or irritate the skin when the hydrogel is removed therefrom.

Because the hydrogels may lose water eventually under ambient conditions, they are preferably stored in a water and gas impermeable container, e.g., a polyfoil packet formed from the laminated plastic conventionally used to store measured amounts of freeze-dried or ground coffee. Sealed envelopes are conventionally produced by heat sealing a pair of sheets of thin plastic around the hydrogel sheet-backing laminate, or by heat sealing the open end of an otherwise sealed packet or envelope formed from a single sheet of the laminate.

If both faces of the hydrogel are covered with a release liner or foil, optionally different liners can be employed, one of which is more readily removable from the hydrogel than the other, e.g., a sheet of polyethylene covering one face and a sheet of "Mylar" plastic covering the other, thereby ensuring that a predetermined face of the film or sheet is exposed first. In some end use applications, one of the faces of the film or sheet can be covered with a conductive liner or foil which is not removable and is used as a conductive member. Other variations will be evident to those skilled in the art.

In another embodiment, a large sheet of a laminate formed from the hydrogel and films of plastic covering its faces, e.g., a film of polyethylene on one face and a film of Mylar on the other, is scored at spaced intervals to produce a plurality of severable units, each for individual use. This scoring can be done either before or after the hydrogel is polymerized and sterilized.

If desired, a plurality of shaped units such as circles, squares or rectangles of the hydrogel with a release liner covering one face of the hydrogel can be "stacked" one upon the other so that a column of units of the hydrogel sheet with both faces covered with a liner or foil is formed. Desirably, in such an arrangement, one side of the release liner has a higher adhesive value than the other, so that only one unit of the hydrogel is removed at a time from the column. Such columns can be conveniently stored in glass jars or aluminum lined paper tube with a moisture impervious cap which form a gas and moisture impervious sealed container. Again, this arrangement can be achieved before the hydrogel is polymerized and sterilized.

As stated above, the hydrogels employed in this invention are characterized by surface adhesiveness, and sufficient cohesiveness to maintain structural integrity when being removed from the skin.

An important feature for adhesive hydrogels such as those of the invention, especially for use in wound management applications, is the hydrogel's absorptive capacity. This property is important because a hydrogel, when placed on the skin, can readily lose its adhesive bond due to perspiration at the skin-gel interface. Moreover, if hydrogel is utilized as a wound dressing it must be capable of absorbing the exudate from the wound. If the hydrogel cannot do so, it will also lose its adhesive bond and move from the site where it was intended to function. For these reasons it is important for the adhesive hydrogel to have good equilibrium or absorption capacity for aqueous liquids. A test method that quantitatively measures the absorption capacity of a cross-linked polymer system is the swelling test.

The swelling test method proceeds in the same manner as the extraction test previously mentioned, up to the point of extraction. The weight of the extracted sheet, with unbound excess water removed from the surface, is divided by the weight of the original sheet to yield the swell ratio (SR). The hydrogels of the present invention, may have an absorption capacity, as measured by the swell ratio (SR), of at least about 5. Thus, the gels can absorb perspiration or exudate up to five times its weight.

The adhesive hydrogels of the invention contain no extraneous or other objectional ingredients. All ingredients have proven bioacceptability on contact with the skin. Normal exudants flow into the matrix of the hydrogels away from the user's skin. The hydrogel's hydrophilic properties eliminate the common requirement for abrasive treatment and/or other skin preparation. The biocompatibility of the hydrogels is expected to be quite favorable because all the ingredients used to prepare the hydrogels are themselves, highly biocompatible.

The hydrogels of the invention do not contain free water. The water in the hydrogel is an integral part of the hydrogel structure and therefore cannot be separated therefrom by physical means such as pressure. Thus, the matrix remains homogeneous under gravity and even at temperatures approaching 0° C.

For ulcers or deep wounds, the present hydrogels are sufficiently viscous to fill in the voids. Conveniently, the gel may be dispensed as a fluid-like material from a syringe or nozzle into the wound, where it reforms as a cohesive gel which facilitates the healing of the wound. The gel protects the wound and permits healing, does not interfere with new tissue growth or development, and is capable of absorbing significant amounts of wound exudate. These gels also have sufficient cohesive strength for subsequent removal from the cavity as an integral plug without interrupting the healing process.

In forming aqueous gel forming polymer mixtures which are useful in the present invention, the polymers and water are combined to provide a mixture. Generally, the formulation is provided in two parts: the first containing the acid containing polymer, and the second containing the first and third polymers. Slow agitation in a device such as a low shear type mixer is employed. Gellation begins immediately and will increase upon standing or with the addition of heat.

These gels can be placed into a syringe or nozzle for dispensing onto the patient. As noted above, the gels can be dispensed as a relatively fluid mass which then forms a cohesive solid in the wound. Alternatively, the material can be extruded in the form of a layer as described above.

EXAMPLES

A number of different formulations were prepared to illustrate the features and advantages of the invention. These formulations are listed in Table I below. For each example, the chitosan derivative was N,O-carboxymethyl chitosan. In addition, with the exception of examples 3 and 4, the balance of each formulation was deionized water. 5 weight percent of glycerine was added to the formulations of Examples 3 and 4 to help solubilize the acid-containing polymer in the water.

TABLE I

| Example | Acid Containing Polymer | Chitosan Derivative | PVP K90 (%) | PEO WSR-205 (%) | NaOH (%) | $CaCl_2$ (%) |
|---|---|---|---|---|---|---|
| 1 | 0.5 | 2.50 | 10 | 0.5 | 0.16 | — |
| 2 | 0.5 | 2.41 | 10 | 0.5 | 0.16 | 0.87 |
| 3 | 2.5 | 2.50 | — | 5.625 | 0.97 | — |
| 4 | 2.5 | 2.41 | — | 5.625 | 0.97 | 0.87 |
| 5 | 2.5 | 2.50 | 10 | 0.5 | 0.792 | — |
| 6 | 2.5 | 2.41 | 10 | 0.5 | 0.792 | 0.87 |
| 7 | 1.25 | 2.50 | 10 | 0.5 | 0.396 | — |
| 8 | 1.25 | 2.41 | 10 | 0.5 | 0.396 | 0.87 |
| 9 | 0.25 | 2.50 | 10 | 0.5 | 0.08 | — |
| 10 | 0.25 | 2.41 | 10 | 0.5 | 0.08 | 0.87 |
| 11 | 0.125 | 2.50 | 10 | 0.5 | 0.04 | — |
| 12 | 0.125 | 2.41 | 10 | 0.5 | 0.04 | 0.87 |
| 13 | 0.5 | 2.50 | 10 | 0.5 | — | — |
| 14 | 0.5 | 2.41 | 10 | 0.5 | — | 0.87 |
| 15 | 1.25 | 2.50 | 10 | 0.5 | — | — |
| 16 | 1.25 | 2.41 | 10 | 0.5 | — | 0.87 |
| 17 | 2.5 | 2.50 | 10 | 0.5 | — | — |
| 18 | 2.5 | 2.41 | 10 | 0.5 | — | 0.87 |
| 19 | 0.5 | 2.50 | 10 | 0.5 | — | — |
| 20 | 0.5 | 2.41 | 10 | 0.5 | — | 0.87 |
| 21 | 1.25 | 2.50 | 10 | 0.5 | — | — |
| 22 | 1.25 | 2.41 | 10 | 0.5 | — | 0.87 |
| 23 | 2.5 | 2.50 | 10 | 0.5 | — | — |
| 24 | 2.5 | 2.41 | 10 | 0.5 | — | 0.87 |
| 25 | 0.25 | 2.50 | 10 | 0.5 | — | — |
| 26 | 0.25 | 2.41 | 10 | 0.5 | — | 0.87 |
| 27 | 0.25 | 2.50 | 10 | 0.5 | — | — |
| 28 | 0.25 | 2.41 | 10 | 0.5 | — | 0.87 |

The following acid containing polymers were used for the above formulations:

Ethylene Maleic Anhydride—Examples 1, 2, and 5–12.

Acrylidone Anionic Copolymer (25% vinyl PVP and 75% acrylic acid)—Examples 3 and 4

Poly(methyl vinyl ether/maleic anhydride) GANTREZ S-95, MW=20,000, Examples 13–18 and 25–26

Poly(methyl vinyl ether/maleic anhydride) GANTREZ S-97, MW=70,000, Examples 19–24 and 27–28

These examples were formulated by mixing the components together at room temperature, and allowing them to stand to form gels. Various properties of the gels were then measured and the results are reported in Table II. The Swell Ratio (SR) was measured

TABLE 2

| Ex. | Initial Physical Characteristics | Swell Ratio ("SR") |
|---|---|---|
| 1 | clear/yellow cohesive resilient gel. Cohesion seemed to increase with time. pH 7.44 | Day 2 after mixing: SR in DI water = 2.42, SR in saline = 1.60; Day 7 after mixing: SR in saline = 2.03 (gel lost resilient quality) |
| 2 | clear/yellow cohesive resilient gel. Cohesion seemed to increase with time. pH 6.86 | Day 1 after mixing: 1 g gel + 5 g saline solution = gel chunks dispersed in saline solution; Day 6 after mixing: SR in saline = 1.52 (gel lost resilient quality) |
| 3 | clear/yellow semi-cohesive, semi-resilient gel. pH 8.34 | — |
| 4 | clear/yellow semi-cohesive, semi-resilient gel. pH 7.97 | — |
| 5 | clear/yellow semi-cohesive, semi-resilient gel. pH 6.57 | — |
| 6 | clear/yellow semi-cohesive, semi-resilient gel. pH 6.15 | — |
| 7 | clear/yellow cohesive resilient gel. Cohesion seemed to increase with time. pH 7 | Day 2 after mixing: 1 g gel + 5 g saline solution = gel chunks dispersed in saline solution |
| 8 | clear/yellow semi-cohesive, semi-resilient gel. pH 6.41 | Day 1 after mixing: 1 g gel + 5 g saline solution = gel chunks dispersed in saline solution |
| 9 | clear/yellow cohesive resilient gel. Cohesion seemed to increase with time. pH 7.84 | Day 2 after mixing: SR in saline = 0.79 (some gel lost to saline solution and gel retained some resilient quality), Day 7 after mixing; SR in saline = 2.56 (gel lost resilient quality) |
| 10 | clear/yellow cohesive resilient gel. Cohesion seemed to increase with time. pH 7.55 | Day 1 after mixing: 1 g gel + 5 g saline solution = gel chunks dispersed in saline solution, Day 6 after mixing: SR in saline = 0.88 (some gel lost to saline solution and gel lost resilient quality) |
| 11 | clear/yellow cohesive resilient gel. Cohesion seemed to increase with time. pH 8.05 | Day 5 after mixing: gel dissolved in saline solution |
| 12 | clear/yellow cohesive resilient gel. Cohesion seemed to increase with time. pH 7.52 | Day 5 after mixing: gel dissolved in saline solution |
| 13 | clear/yellow cohesive resilient gel. Cohesion seemed to increase with time. pH 7.47 | Day 1 after mixing: 1 g gel + 5 g saline solution = gel chunks dispersed in saline solution, Day 5 after mixing: SR in saline = 2.35 (gel lost resilient quality) |
| 14 | clear/yellow non-cohesive gel. pH 6.03 | Day 1 after mixing: 1 g gel + 5 g saline solution = gel chunks dispersed in saline solution, |

TABLE 2-continued

Results

| Ex. | Initial Physical Characteristics | Swell Ratio ("SR") |
|---|---|---|
| | | Day 5 after mixing: gel broke up in saline |
| 15 | clear/yellow non-cohesive gel. pH 4.99 | Day 1 after mixing: 1 g gel + 5 g saline solution = gel chunks dispersed in saline solution |
| 16 | clear/yellow non-cohesive gel particles in liquid. pH 4.52 | Day 1 after mixing: 1 g gel + 5 g saline solution = gel chunks dispersed in saline solution |
| 17 | clear/yellow non-cohesive sticky gel. pH 4.60 | — |
| 18 | clear/yellow non-cohesive gel. pH 5.12 | — |
| 19 | clear/yellow cohesive resilient gel. Cohesion seemed to increase with time. pH 6.90 | Day 1 after mixing: SR in saline = 1.63, Day 5 after mixing: SR in saline = 1.58 (gel retained cohesive and resilient qualities) |
| 20 | clear/yellow mostly-cohesive gel. pH 6.15 | Day 1 after mixing: 1 g gel + 5 g saline solution = gel chunks dispersed in saline solution, Day 5 after mixing: SR in saline = 1.56 (gel retained cohesive and resilient qualities) |
| 21 | clear/yellow semi-cohesive, semi-resilient gel. pH 5.06 | 1 g gel + 5 g saline solution (for 20 hours): gel chunks dispersed in saline solution |
| 22 | clear/yellow non-cohesive sticky gel. pH 4.20 | 1 g gel + 5 g saline solution (for 20 hours): gel weight = 1.48 g and gel retained some resilient quality |
| 23 | did not fully mix together. pH 4.60 | — |
| 24 | did not fully mix together. pH 372 | — |
| 25 | clear/yellow cohesive resilient gel. Cohesion seemed to increase with time. pH 7.23 | Day 1 after mixing: SR in saline = 1.51 (gel lost cohesive quality) |
| 26 | clear/yellow cohesive resilient gel. Cohesion seemed to increase with time. pH 7.24 | Day 1 after mixing: SR in saline = 1.90 (gel lost cohesive quality) |
| 27 | clear/yellow cohesive resilient gel. Cohesion seemed to increase with time. pH 7.44 | Day 1 after mixing: SR in saline = 2.27 (gel lost cohesive quality) |
| 28 | clear/yellow cohesive resilient gel. Cohesion seemed to increase with time. pH 7.04 | Day 1 after mixing: gel dispersed in saline solution |

The formulations of Examples 3–6 provided satisfactory gels. For Examples 7–10, calcium chloride appears to have reduced both the cohesivity and swell ratio, while decreasing the amounts of the acid containing polymer increased both the cohesivity of the gel and the swell ratio in saline. These properties also increased as the time after mixing increased.

For the formulations of Examples 13–28, as the molecular weight of the acid containing polymer increases, the cohesivity of the gel increases but the swell ratio decreases. Lower concentrations of the acid containing polymer increase the handling characteristics, cohesivity and swell ratios of the gels. These properties also increased over time after mixing.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A gel forming system comprising an aqueous mixture of at least three different components including a first component of at least one hydrophilic water-soluble polymer of polyethylene oxide, polyvinylpyrrolidone or mixtures thereof, said first component being present in an amount sufficient to increase the initial viscosity of the mixture and impart adhesivity properties thereto; a second component of an acid-containing polymer comprising poly(vinyl pyrrolidone/acrylic acid), poly(methyl vinyl ether/maleic anhydride), poly(ethylene/maleic anhydride) or poly(acrylic acid) in an amount which contains sufficient acid or acid-forming groups to provide crosslinking capabilities or intermolecular hydrogen bonding with the first component to increase the cohesiveness of the mixture over time; a third component of an amino-containing polymer for accepting protons from the second component and increasing the cohesiveness of the mixture; and water; wherein the system has a pH in the range of between about 5.5 and 8.5, and the mixture is initially combined in a relatively fluid state before subsequently forming a cohesive gel structure.

2. The gel forming system of claim 1 wherein the first component is present in an amount of between about 3 and 35% by weight of the system.

3. The gel forming system of claim 2 wherein the first component is a hydrophilic water-soluble polymer mixture of poly(vinyl pyrrolidone) and poly(ethylene oxide) in a weight ratio of between about 10/1 and 25/1 wherein the poly(vinyl pyrrolidone) is present in an amount of between about 10 and 25% by weight of the system.

4. The gel forming system of claim 2 wherein at least a portion of the hydrophilic water soluble polymer of the first component is crosslinked.

5. The gel forming system of claim 1 wherein the second component is present in an amount of between about 0.1 and 10% by weight of the system.

6. The gel forming system of claim 5 wherein a portion of the acid or acid-forming groups of the second component are neutralized to reduce the crosslinking capabilities of the component.

7. The gel forming system of claim 6 wherein a portion of the acid or acid-forming groups of the second component are neutralized by conversion to an acid salt, by conversion to an amide, or by the incorporation of anions which interfere with the hydrogen bonding capabilities of the second component.

8. The gel forming system of claim 1 wherein the third component is present in an amount of between about 0.5 and 5% by weight of the system and comprises a compound which contains free or substituted amino groups.

9. The gel forming system of claim 8 wherein a portion of the amino groups of the third component are substituted with a water soluble group or a double bond to reduce the crosslinking capabilities of the third component.

10. The gel forming system of claim 8 wherein the third component is a polysaccharide, alginic acid, hyaluronic acid, a carrageenan, agar, or a polyamino acid or derivative thereof.

11. The gel forming system of claim 10 wherein the third component is poly-L-lysine or a polysaccharide based upon glucosamine and gluconic acid derivatives.

12. The gel forming system of claim 10 wherein the third component is chitosan, a chitosan derivative or a glycosamino glycan.

13. The gel forming system of claim 12 wherein the third component is N,O-carboxymethyl chitosan, N-carboxymethyl chitosan, N,O-carboxymethyl chitosan or heparin.

14. A gel forming system which comprises an aqueous mixture of a first component of at least one water-soluble polymer in an amount sufficient to increase the initial viscosity of the mixture and impart adhesivity properties thereto; a second component of a acid-containing polymer; a third component of an amino-containing polymer; a crosslinked hydrophilic polymer in an amount sufficient to form an interpenetrating network in the mixture; and water; wherein the system has a pH in the range of between about 5.5 and 8.5 and the second and third components are each present in sufficient amounts which, in combination, increase the cohesiveness of the mixture over time, such that the mixture can be initially combined in a relatively fluid state and subsequently forms a cohesive gel structure.

15. The gel forming system of claim 1 which further comprises one or more additional uniformly dispersed additives selected from the group consisting of preservatives, stabilizers, fire retardants, pigments, refractive particles, bactericides, antibiotics, cosmetics, moisturizers, pharmacologic agents and mixtures thereof.

16. The gel forming system of claim 15 wherein each additive which is included is present at a concentration of about 0.001 to about 3% by weight of the system.

17. The gel forming system of claim 15 wherein the pharmacologic agent is epidermal growth factor, platelet growth factor or transforming growth factor$\beta_1$.

18. The gel forming system of claim 1 which further comprises a humectant for increasing the solubility of the first or second component in the mixture.

19. The gel forming system of claim 18 wherein the humectant is glycerol, propylene glycol, or poly(ethylene glycol), N-methyl pyrrolidone, N-ethyl pyrrolidone, diacetone alcohol, γ-butyryl lactone, ethyl lactate or combinations thereof.

20. The gel forming system of claim 19 wherein the humectant is present at a concentration of about 1 to about 40% by weight of the system.

21. The gel forming system of claim 19 wherein the humectant is present at a concentration of about 5 to about 20% by weight of the system.

22. The gel forming system of claim 1 which further comprises a water-soluble electrolyte in an amount effective to reduce the transverse electrical resistance of the gel to an impedance at 60 Hz of less than about 1000 ohms.

23. The gel forming system of claim 22 wherein the water-soluble electrolyte is present in an amount effective to reduce the impedance of the gel to less than about 100 ohms.

24. The gel forming system of claim 22 wherein the water-soluble electrolyte is an inorganic or organic salt.

25. The gel forming system of claim 24 in which the water-soluble electrolyte is a potassium salt, a sodium salt, a magnesium salt, a calcium salt or a mixture thereof.

26. The gel forming system of claim 22 wherein the water-soluble electrolyte is present in an amount of about 0.1 to about 10% by weight of the system.

27. A gel forming system comprising an aqueous mixture of a first component comprising at least one water-soluble polymer of polyethylene oxide in an amount sufficient to increase the initial viscosity of the mixture and impart adhesivity properties thereto; a second component comprising poly(vinyl pyrrolidone/acrylic acid), poly(methyl vinyl ether/maleic anhydride), poly(ethylene/maleic anhydride) or poly(acrylic acid) in an amount which contains sufficient acid or acid-forming groups to provide crosslinking capabilities or intermolecular hydrogen bonding with the first component to increase the cohesiveness of the mixture over time; a third component of a polysaccharide for accepting protons from the second component and increasing the cohesiveness of the mixture; and water; wherein the system has a pH in the range of between about 5.5 and 8.5, and the mixture can be initially combined in a relatively fluid state before subsequently forming a cohesive gel structure.

28. The gel forming system of claim 27 wherein at least a portion of the first component is crosslinked and wherein the first component is present in an amount of between about 3 and 35% by weight of the system.

29. The gel forming system of claim 28 wherein the second component is poly(vinyl pyrrolidone/acrylic acid) and is present in an amount of between about 0.1 and 10% by weight of the system.

30. The gel forming system of claim 29 wherein the third component is a polysaccharide which contains free or substituted amino groups, a portion of which are substituted with a water soluble group or a double bond to reduce the crosslinking capabilities of the polysaccharide and the third component is present in an amount of between about 0.5 and 5% by weight of the system.

31. A gel forming system comprising an aqueous mixture of a first component of at least one water-soluble polymer of a hydrophilic water-soluble polymer of polyethylene oxide, polyvinylpyrrolidone or mixtures thereof and is present in an amount of between about 3 and 35% by weight of the mixture to increase the initial viscosity of the mixture and impart adhesivity properties thereto; a second component of a acid-containing polymer comprising poly(vinyl pyrrolidone/acrylic acid), poly(methyl vinyl ether/maleic anhydride), poly(ethylene/maleic anhydride) or poly(acrylic acid) in an amount of between about 0.1 and 10% by weight of the system and contains sufficient acid or acid-forming groups to provide crosslinking capabilities or intermolecular hydrogen bonding with the first component to increase the cohesiveness of the mixture over time; a third component of an amino-containing polymer comprising a polysaccharide, alginic acid, hyaluronic acid, a carrageenan, agar, or a polyamino acid or derivative thereof in an amount of between about 0.5 and 5% by weight of the system and comprises a compound which contains free or substituted amino groups for accepting protons from the second component and increasing the cohesiveness of the mixture; and water; wherein the system has a pH in the range of between about 5.5 and 8.5 and the second and third components are each present in amounts which, in combination, increase the cohesiveness of the mixture over time, such that the mixture can be initially combined in a relatively fluid state and subsequently forms a cohesive gel structure.

* * * * *